United States Patent [19]

Anderson et al.

[11] 4,357,282

[45] Nov. 2, 1982

[54] PREPARATION OF FLUOROCARBONYL COMPOUNDS

[75] Inventors: Daniel G. Anderson; David C. England; Alwin S. Milian, Jr., all of Wilmington, Del.

[73] Assignee: E. I. Du Pont de Nemours and Company, Wilmington, Del.

[21] Appl. No.: 250,134

[22] Filed: Apr. 3, 1981

Related U.S. Application Data

[63] Continuation-in-part of Ser. No. 71,684, Aug. 31, 1979.

[51] Int. Cl.³ .............................................. C07C 51/58
[52] U.S. Cl. ............................ 260/544 F; 260/465.7;
560/174; 560/177; 560/129; 560/192; 562/577;
564/209; 568/39; 568/43; 568/301; 568/383;
568/395; 568/405; 568/676
[58] Field of Search ................... 260/544 F, 465.7;
568/405, 301

[56] References Cited

FOREIGN PATENT DOCUMENTS 1143930 2/1969 United Kingdom ............ 260/544 F

*Primary Examiner*—Paul J. Killos
*Attorney, Agent, or Firm*—James A. Costello

[57] ABSTRACT

Fluorinated carbonyl compounds are prepared by contacting a fluorinated methyl or ethyl ether containing at least one methoxylated carbon atom-containing group selected from: $-CF_2OR^3$, $=CFOR^3$,

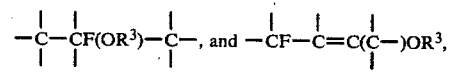

wherein $R^3$ is $CH_3$ or $C_2H_5$, with a catalyst selected from:

$SbX_5$, $TaX_5$, $NbX_5$, $AsX_5$, $BiX_5$, $TiX_4$, $ZrX_4$, $HfX_4$, $FeX_3$, mixtures of $SbX_3$ and $SbX_5$, $ZM'X'_6$, and mixtures of $ZM'X'_6$ and $M'X_5$ where X, independently, is F, Cl, Br or I, X' is F or Cl; and Z is H, NO, $O_2$, alkali metal or $NY_4$ where Y, independently, is H or alkyl of 1 to 6 carbon atoms, and M' is Sb or As at a temperature of $-20°$ to $200°$ C.

12 Claims, No Drawings

PREPARATION OF FLUOROCARBONYL COMPOUNDS

CROSS-REFERENCE TO RELATED APPLICATION

This is a continuation-in-part application of copending application bearing U.S. Ser. No. 071,684, filed Aug. 31, 1979.

BACKGROUND OF THE INVENTION

This invention relates to a catalytic process for preparing fluorine-containing carbonyl compounds from certain fluorinated ethers.

Knunyants, et al., Isvestiya Akademii Nauk SSSR, Seriya Khimicheskaya No. 8, pages 1389 to 1393, August, 1963, discloses the reaction of $AlCl_3$ with the fluorinated ethyl ether $(CF_3)_2CHCF_2OC_2H_5$ to form $(CF_3)_2CHCOF$ in 24% yield;

British Pat. No. 1,143,930 discloses the $CaCl_2$ catalyzed preparation of acid fluorides from ethers having a fluorine atom and a bromine atom on the carbon next to the ether oxygen;

U.S. Pat. No. 4,131,740 discloses preparation of methyl and ethyl difluoro(fluoroformyl)acetates by reacting the corresponding alkoxytetrafluoropropionates with $SO_3$;

U.S. Pat. No. 4,127,731 and Japanese Application No. J53/040708 disclose alcoholysis of a lactone and a diacyl fluoride, respectively, to prepare the compounds $ROOC-(CF_2)_{n-1}COF$ and $ROOC-A-COF$;

England et al. J. Fluorine Chem., 3, 69, 1973, disclose the reaction:

$$CF_3CFHCF_2OCH_3 + SO_3 \rightarrow CF_3CFHCOF + CH_3OSO_2F;$$

Lovelace et al., in "Aliphatic Fluorine Compounds," Reinhold, pages 2 and 7 to 10 (1958), have disclosed $SbF_5$, $SbCl_5$, $SbF_3$, $SbF_3Cl_2$, $SbF_2Cl_3$, mixtures of HF and $SbF_5$, $SbCl_5$ or $SbF_3Cl_2$, mixtures of $SbF_3$ and $SbCl_5$ or $SbF_3Cl_2$, and $TiF_4$ as catalysts for fluorinating organic compounds;

Olah et al., in Advances In Fluorine Chemistry, 7, 69 (1973) have disclosed using $HSbF_6$ in the protonation of olefins;

Krespan et al., in Fluorine Chemistry Reviews, 1, 147 (1967) have disclosed $SbF_5$ as a catalyst in the formation of hexafluoroacetone from hexafluoropropene oxide;

U.S. Pat. No. 3,948,761 discloses $TaF_5$ and $NbF_5$, in combination with HF, as isomerization catalysts;

Generally known in the art are $SbCl_5$, $AlCl_3$, $TiCl_4$ and $SnCl_4$ as Lewis acid catalysts for acylation reactions.

SUMMARY OF THE INVENTION

A process is provided for preparing fluorinated carbonyl compounds which comprises contacting a fluorinated methyl or ethyl ether containing at least one methoxylated carbon atom-containing group selected from the group consisting of $-CF_2OR^3$, $=CFOR^3$,

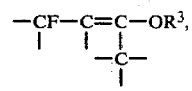

-continued

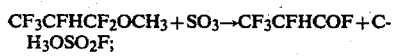

wherein $R^3$ is $CH_3$ or $C_2H_5$, with a catalyst selected from the group consisting of $SbX_5$, $TaX_5$, $NbX_5$, $AsX_5$, $BiX_5$, $TiX_4$, $ZrX_4$, $HfX_4$, $FeX_3$, mixtures of $SbX_3$ and $SbX_5$, $ZM'X'_6$, and mixtures of $ZM'X'_6$ and $M'X_5$ where M' is Sb or As; X, independently, is F, Cl, Br or I; X' is F or Cl; and Z is H, NO, $O_2$, alkali metal or $NY_4$ where Y, independently, is H or alkyl of 1 to 6 carbon atoms.

The products from ethers containing terminal groups $-CF_2OR^3$ or $=CFOR^3$ are acyl fluorides. The products from internal ethers containing the groups

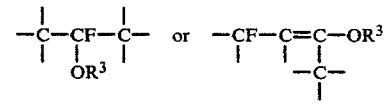

are ketones.

Preferred ethers in the practice of the present invention are drawn from those containing the above groups and including the following:

Class 1. Saturated terminal ethers of the formula

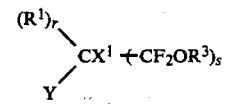

wherein $X^1$ is $-H$ or $-F$, Y is $-F$ or $-CF_3$;
r is 0 or 1;
s is 1 or 2 and $r+s=2$;
$R^1$ is $-F$, $-Cl$, $-Br$, $-SO_2F$, $-COF$, $-OCH_3$, $-CN$, $-CO_2H$, $-CO_2CH_3$, $-OC_6F_5$, $-OR$, $-SR$, or $-R$, where R is a fluorinated alkyl of 1 to 8 carbon atoms, linear or branched, interruptable with ether oxygen or keto groups, and optionally containing functional substituents selected from the group consisting of $-F$, $-Cl$, $-Br$, $-SO_2F$, $-COF$, $-OCH_3$, $-CN$, $-CO_2H$, $-CO_2CH_3$, and $-OC_6F_5$; and
$R^3$ is as defined above.

Class 1 fluoroethers provide carbonyl compounds which are acid fluorides:

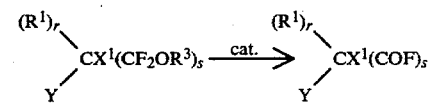

Class 2: Saturated terminal ethers of the formula $Z_m(CFH-CF_2OR^3)_2$ where Z is $-O-$, $-S-$, or $-(CF_2)_n-$ where n is 1 to 8, m is 0 or 1, and $R^3$ is defined above.

Class 2 fluoroethers provide acid fluorides:

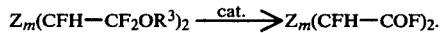

Class 3: Terminally unsaturated terminal ethers of the formula

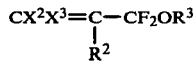

wherein $X^2$ and $X^3$ are the same or different and are selected from —H, —F, or —Cl, $R^2$ is perfluoroalkyl of 1 to 8 carbon atoms and $R^3$ is as defined above.

Class 3 fluoroethers provide acid fluorides:

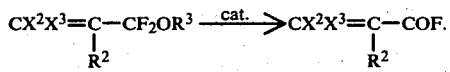

Class 4: Internally unsaturated terminal ethers of the formula

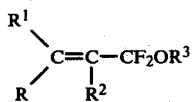

wherein R, $R^1$, $R^2$ and $R^3$ are as defined above.
These fluoroethers provide acid fluorides:

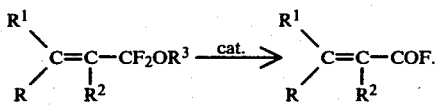

Class 5: Internally unsaturated terminal ethers of the formula

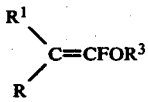

wherein R, $R^1$ and $R^3$ are as defined above. These fluoroethers provide acid fluorides:

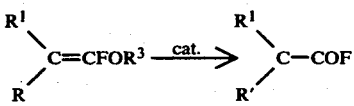

where R' is the same as R except that alkyl is alkylidene.

Class 6: Saturated internal ethers of the formula

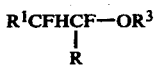

wherein R, $R^1$ and $R^3$ are as defined above. These fluoroethers provide ketones:

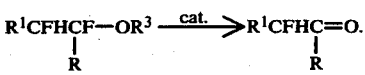

Class 7: Unsaturated internal ethers of the formula

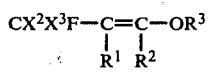

wherein $X^2$, $X^3$, $R^1$, $R^2$ and $R^3$ are as defined above. These fluoroethers provide ketones:

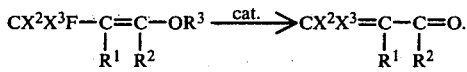

Fluoroethers which are operable in the present invention are numerous and include, but are not restricted to, mono- and polyethers of Classes 1 to 7. For example, the following additional classes of ethers containing the specified groups also provide carbonyl compounds when contacted with the catalysts of this invention.

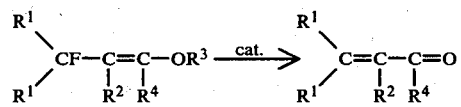

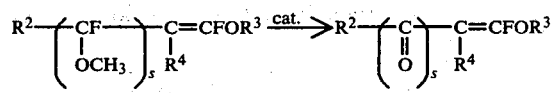

In these formulae the symbols $R^1$, $R^2$, $R^3$ and s have the meaning defined above; $R^4$, independently, has the same meaning as $R^2$.

In the practice of the present invention, fluorinated ethers of Classes 1 to 7 defined above are contacted with a small quantity (normally not exceeding 30 mol % of the reactant ether) of a suitable catalyst listed above. The catalyst can be any one of the above catalysts or any mixture of two or more of the above catalysts. For example, mixtures of $ZM'X'_6$ with $M'X_5$ can contain 0 to about 100 moles of $M'X_5$ per mole of $ZM'X'_6$. Preferred components in such mixtures are $HSbX'_6$ and $SbX'_5$ where X' is F or Cl. Mixtures of $SbX_3$ with $SbX_5$ can contain about 0.01 to 100 moles of $SbX_3$ per mole of $SbX_5$. Any of the catalysts lists above, particularly those which are liquid at ordinary temperatures, such as $SbF_5$, $SbCl_5$ and $TiCl_4$, can be supported on an inert substrate such as graphite.

When the Class 1 ethers methyl/ethyl tetrafluoro-3-methoxy propionate or methyl/ethyl tetrafluoro-3-ethoxy propionate are employed, operable catalysts include $AlCl_3$, $AlBr_3$ and $AlI_3$ in addition to those listed above.

The contacting can be carried out over a wide range of temperatures from about $-20°$ C. to $200°$ C. depending on the starting ether and catalyst. The preferred temperature is about $-10°$ to $150°$ C. Especially preferred ethers, methyl 2,2,3,3,-tetrafluoro-3-methoxypropionate and 3-methoxytetrafluoropropionitrile, both Class 1 ethers, are preferably contacted at about $60°$ to $140°$ C. Use of a solvent is optional; preferably a reaction product serves as a solvent. Freon® E3, a commercial product having the formula, $F[CF(CF_3)CF_2O]_3CHFCF_3$, and Rimar® 101, a commercial mixture of perfluorinated alkyl furan and pyran, are also suitable solvents.

The reaction can be carried out in a sealed tube or other closed container. The reaction product is isolated by distillation. Operation at atmospheric pressure is preferred, but reaction in closed vessels, in which an autogeneous pressure of up to 100 atmospheres may develop, is satisfactory.

In preparing fluorinated carbonyl compounds such as methyl difluoro(fluoroformyl)acetate (2 in Example 2) from a fluoroether of Class 1, it has previously been necessary to employ a stoichiometric amount of sulfur trioxide ($SO_3$) which produced a corrosive and poisonous by-product, $CH_3OSO_2F$. The process of the present invention requires relatively small amounts of the catalyst compounds or mixtures described above, the amount normally not exceeding 30 mol % of the reactant ether, often much less. Moreover, the by-products, $CH_3X$ and $C_2H_5X$, are relatively inert and easily separated from the carbonyl product. Product yields in the present process are generally over 60%. Yields of over 95% of compound 2 have been obtained by reacting methyl 2,2,3,3,-tetrafluoro-3-methoxypropionate, 1, in the presence of the catalysts of this invention (Example 2).

Although it is in no way intended that the process of this invention be limited to any particular mechanism, it is believed that the conversion of fluoroethers of Classes 1 to 7 defined above to carbonyl compounds involves chemical interaction between said fluoroethers and catalyst, in consequence of which said catalyst abstracts fluorine from the fluoroether. The following hypothetical equation involving a pentavalent metal chloride, for example, $SbCl_5$, is illustrative:

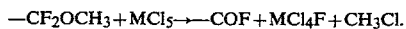
—$CF_2OCH_3+MCl_5\rightarrow$—$COF+MCl_4F+CH_3Cl$.

The fluorinated specie, $MCl_4F$, in subsequent encounters with more fluoroether, may or may not become progressively more fluorinated; thus

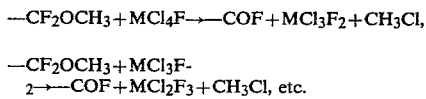
—$CF_2OCH_3+MCl_4F\rightarrow$—$COF+MCl_3F_2+CH_3Cl$,

—$CF_2OCH_3+MCl_3F_2\rightarrow$—$COF+MCl_2F_3+CH_3Cl$, etc.

and/or

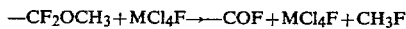
—$CF_2OCH_3+MCl_4F\rightarrow$—$COF+MCl_4F+CH_3F$ may occur. Obviously, fully fluorinated compounds remain compositionally unchanged as in the final equation above; for example,

—$CF_2OCH_3+MF_5\rightarrow$—$COF+MF_5+CH_3F$.

Although catalytic materials can be added in fully or partially fluorinated form, it is preferable for economic reasons to introduce, as the starting catalyst, unfluorinated materials such as chlorides.

Material suitable for introduction as catalysts in the practice of this invention include those broadly characterized as containing one or more species, $M_xQ_y$, wherein M is a selected metal of valence y and Q is a selected radical of valence x, which can react with fluorinated ethers as illustrated above, e.g.,

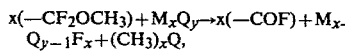
$x(-CF_2OCH_3)+M_xQ_y\rightarrow x(-COF)+M_xQ_{y-1}F_x+(CH_3)_xQ$, and whose fluorinated reaction products can similarly react with fluoroether thus maintaining catalytic activity, as previously discussed.

Catalysts meeting the above description also include so-called complex acids and salts having the formula, $ZM'X'_6$, where the symbols are defined as above, e.g., $NOM'X'_6$, $O_2M'X'_6$, $HM'X'_6$ and alkali metal, ammonium or quaternary ammonium salts of $HM'X'_6$. The active catalytic moiety within such complex compounds is believed to be $M'X'_5$ or the $M'X'_6$-anion. The complex compounds may have improved solubility, viscosity and the like. Complex acids and salts of metal halides disclosed herein, other than those of Sb and As, are also expected to be suitable catalysts provided they and their more fluorinated products have some solubility in the reaction media.

Instances have been discovered wherein certain metal chlorides, namely $SnCl_4$, $WCl_6$, $MoCl_5$ and $GaCl_3$, while initially active in effecting the conversion of fluoroethers to carbonyl compounds, becomes less active, the conversion of ether becoming progressively more sluggish. It is believed that fluorinated derivatives of these metal chlorides produced in the reaction react more slowly with fluoroether, probably because of reduced solubility.

$AlCl_3$, $AlBr_3$ and $AlI_3$ effectively catalyze the conversion of Class 1 ethers methyl/ethyl tetrafluoro-3-methoxypropionate and methyl/ethyl tetrafluoro-3-ethoxypropionate to methyl/ethyl difluoro(fluoroformyl)acetate (Example 2N, 2U, 2V), but behave unpredictably with other fluoroethers, giving poor yields of carbonyl product in some instances (Comparative Examples 1 and 2), with relatively short-lived catalytic activity. This behavior may arise from fluorination of the aluminum halides during reaction; $AlF_3$ is insoluble and inoperable as a catalyst in the described fluoroether conversions.

In a preferred embodiment of the present invention, HF is added to $SbF_5$, in an amount up to a molar ratio of about 1:1, preferably 0.01:1 to 0.5:1. HF combines with $SbF_5$ in equimolar amounts to form hexafluoroantimonic acid $HSbF_6$, with the result that the viscosity of the normally viscous, polymeric liquid $SbF_5$ is very substantially reduced without significant loss of catalytic activity. Mixtures of $SbF_5$ and $HSbF_6$, formed as just described, are considerably easier to transfer, for example, by pump or syringe, than pure $SbF_5$.

In another preferred embodiment of the invention, graphite impregnated with $SbX_5$ where X is as defined above, up to about 60% by weight, is used to catalyze the conversion of fluoroethers to fluorinated carbonyl compounds by allowing fluoroether vapor to contact said catalyst contained in a stirred-bed reactor.

Fluorinated ethers operable in the present invention are prepared by known methods including the addition of methanol to terminal and internal fluoroolefins, unsaturated fluoroethers, and terminal diolefins; reaction of alkali metal alkoxides with fluoroolefins; and reaction of unsaturated fluoroethers with reagents such as $COF_2$ to produce saturated, functional ethers (Fawcett et al. *J. Am. Chem. Soc.*, 84, 4280 (1962), e.g.:

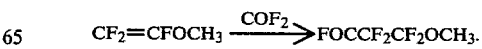
$CF_2=CFOCH_3 \xrightarrow{COF_2} FOCCF_2CF_2OCH_3$.

The fluorinated carbonyl compounds prepared in accordance with this invention are all useful. The acid fluoride products of Class 1 to 5 ethers can be reacted with hexafluoropropene oxide (HFPO) by known methods; see, for example, U.S. Pat. No. 3,250,808, to form adducts, e.g.:

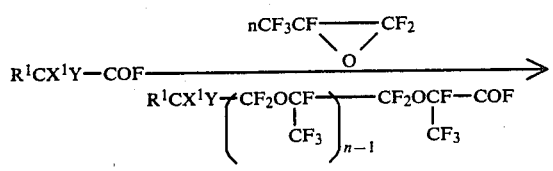

where n is 1 to 6 and $R^1$, $X^1$ and Y are as defined above. Said adducts can be converted to polymerizable vinyl ethers by pyrolysis, preferably in the presence of an alkali metal carbonate or phosphate:

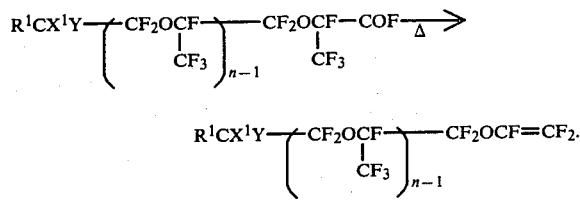

Said vinyl ethers as well as the terminally unsaturated acid fluorides prepared from Class 3 and Class 7 ethers can be copolymerized with suitable ethylenically unsaturated olefins such as tetrafluoroethylene, vinyl fluoride, vinylidene fluoride, hexafluoropropylene, perfluoro(alkylvinyl)ethers, chlorotrifluoroethylene and the like.

Saturated ketones can be converted to acid fluorides by the action of HFPO in the presence of an alkali metal fluoride (U.S. Pat. No. 3,274,239); e.g.:

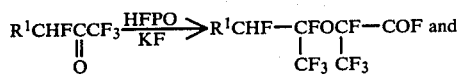

said acid fluorides can be converted to copolymerizable vinyl ethers by pyrolysis as described above:

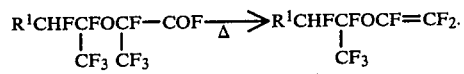

The following Examples illustrate the invention. All temperatures are in degrees Celsius. All parts and percentages are by weight unless otherwise specified.

EXAMPLE 1

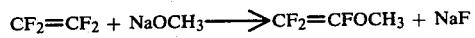

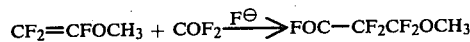

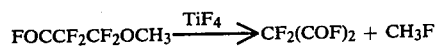

The compound, 3-Methoxyperfluoropropionyl fluoride, (I, 178 g) prepared as shown above, and titanium tetrafluoride (189 g) were heated in a 2250 ml stainless steel cylinder at 175° for 72 h. The cylinder was allowed to cool to room temperature and the volatile gases were transferred under a nitrogen atmosphere to a round bottomed flask immersed in a Dry Ice-methanol bath and connected to a low temperature still. Gas evolved was characterized by infrared as methyl fluoride. There was distilled 111 g (77%) of perfluoromalonyl fluoride (II), b.p. −9°.

EXAMPLE 2

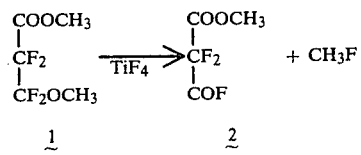

Methyl-2,2,3,3-tetrafluoro-3-methoxypropionate (1, see U.S. Pat. No. 2,988,537; 21 g) and 1 g of TiF$_4$ were sealed in a heavy-walled glass tube and heated in a steam bath overnight. The tube was cooled in liquid nitrogen, opened and the contents vaporized and condensed into a still pot cooled in liquid nitrogen. Distillation in a low-temperature still gave 3.5 g of methyl fluoride (characterized by infrared and condensed into a frozen methanol trap) and 11.2 g (65%) of methyl difluoro(fluoroformyl)acetate (2).

The above experiment was repeated using 12.8 g of SbF$_5$ as catalyst in place of the TiF$_4$. There was isolated 2 g of CH$_3$F and 13.1 g (76%) of 2.

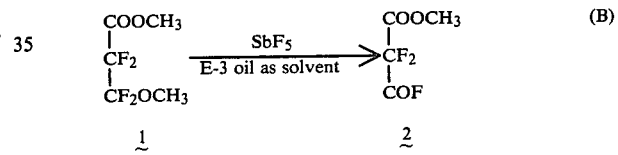

E-3 is CF$_2$CF$_2$CF$_2$OCF(CF$_3$)CF$_2$OCF(CF$_3$)CF$_2$OCF(CF$_3$)H b.p. 152°.

To 15 cc of E-3 oil under N$_2$ in a still pot was added 2.5 g of SbF$_5$ and then dropwise with stirring 23 g of 1. After a slight exotherm (38°), the pot was heated and evolution of CH$_3$F was vigorous at 60°. There was distilled 16 g (84.7%) of 2. b.p. 82°.

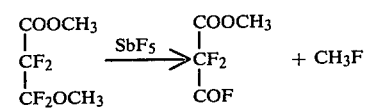

The reaction was run in a 100-ml 3-neck pot with thermometer and dropping funnel and attached to an 18" spinning band still. A Dry Ice-acetone trap was attached to the still. The system was evacuated, flushed with nitrogen and 25 ml (34 g) of 2 added as solvent under nitrogen to the still pot, followed by 1.6 g of antimony pentafluoride.

The product 2 was then heated to reflux (82°) and 1 was added through the dropping funnel. There was immediate evolution of methyl fluoride and 1 was added at about the same rate as 2 was collected from the still.

In about 2 h after adding 430.9 g of 1, the temperature in the pot rose to 130° indicating that the catalyst was no longer active and 1 began to appear in the distillate. There was recovered 61.1 g of 1 and 333 g of 2, including 18 g which had been carried into the Dry Ice trap by the methyl fluoride evolved. Therefore, 369.8 g of 1 was converted by 1.6 g of SbF5 to 299 g of 2 (allowing for 34 g charged to pot). The yield was 98.5%.

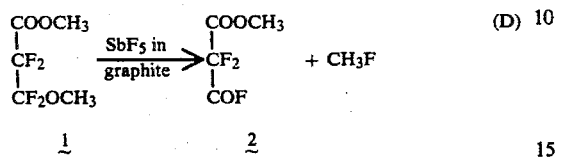

(D)

To 4 g of SbF5 in graphite (46%, from Alpha Division of Ventron Corporation) under nitrogen in a still pot was added 35 g of 1. The mixture was heated and methyl fluoride was evolved, beginning about 80°. There was distilled 25.4 g (88.5%) of 2.

When less catalyst was used (70 g of 1 with 1 g of catalyst) the reaction went well but required a higher temperature of about 112°.

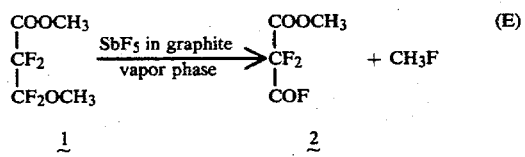

(E)

A stirred-bed reactor was used, consisting of a vertically mounted quartz tube 2.5 cm in diameter×46 cm long with a motor-driven stainless steel screw down the center. Two inlets at the top of the tube admitted a slow stream of nitrogen and a 50 ml hypodermic syringe driven by a Sage pump. The tube was heated by a split-type electric furnace. Off-gases were passed through the Dry Ice-acetone cooled traps. The tube was packed with 46 g of SbF5 in graphite (46% from the Alpha Division of Ventron Corporation).

From 59 g of 1 (b.p. 135°) passed over the stirred bed at 150°, there was obtained, by distillation of material collected in the traps, 31 g (64.6%) of 2 (b.p. 82°) and a residue of 4.5 g. The residue contained $CF_2(COOCH_3)_2$ characterized by gas chromatography.

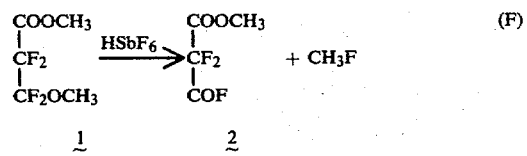

(F)

Hexafluoroantimonic acid (HSbF6) was prepared by cooling in an ice bath 37.15 g (0.171 m) of antimony pentafluoride (SbF5) in a plastic bottle, adding 3.48 g (0.174 m) of hydrogen fluoride (HF) and mixing well.

A 100-ml 3-neck flask was fitted with a thermometer, dropping funnel and a 15-cm unpacked still head with water condenser and an ice-cooled receiver. The system was evacuated, flushed with nitrogen and about 50 ml (67 g) of 2 was added to the flask, followed by 0.89 g of hexafluoroantimonic acid.

The solution was then heated to reflux and 1 was added dropwise at about the same rate as 2 was distilled into the receiver. The initial pot temperature dropped from 87° to 80° and then rose slowly until addition of 1 (211.5 g total) was stopped at a pot temperature of 104°. Distillation ceased when a pot residue of 5.5 g remained (contained $CF_2(COOCH_3)_2$) and 236 g had been collected in the receiver. By gas chromatographic analysis the distillate was 96.8% of 2 and 3.2% of 1. Therefore, the yield, allowing for recovered 1 (7.5 g) and 67 g of 2 used as solvent, was 161.4 g of 2 (96.4%).

Pure antimony pentafluoride is a viscous polymeric liquid, very difficult to transfer, e.g., by hypodermic syringe. When mixed with hydrogen fluoride, even in small amounts, HSbF6 is formed and polymeric chains are destroyed decreasing viscosity. Antimony pentafluoride, HSbF6, and their mixtures are equivalent in catalytic activity for the above reaction. In addition to the pure compounds, catalytic quantities from three 1000-g batches of SbF5 containing respectively 5, 20 and 25 g of hydrogen fluoride to reduce viscosity have been used successfully.

(G) Using the apparatus described in part 2(F), 2.5 g of TiF4 was charged to the still pot followed by 66 g of 1. On heating and stirring, methyl fluoride was evolved and 2 was collected from the still. Heating was continued until only a small residue remained in the still pot which was then cooled and 24 more grams of 1 was added. After this conversion, another 65-g charge of 1 was added to the residue in the still and the reaction continued. A total of 155 g of 1 was converted to 108 g (85%) of 2 from the initial 2.5 g of titanium tetrafluoride charged.

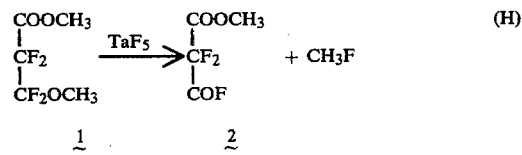

(H)

A mixture of 0.62 g of TaF5 (tantalum pentafluoride) and 89 g of 1 was stirred and heated in a 100-ml 3-neck flask attached to a spinning band still and fitted with a thermometer and magnetic stirrer. Methyl fluoride began coming off around 100°, and the contents of the flask refluxed at 110°, while 2 was collected at a heat temperature of 70° to 80° depending on the rate of methyl fluoride evolution. A total of 65 g (87%) of 2 was collected and then 7 g of $CF_2(CO_2CH_3)_2$ (methyl difluoromalonate) was distilled under vacuum.

Maximum pot temperature was 150°. After cooling the pot, an additional 81 g of 1 was added to the residue without more catalyst. Heating to 130° caused methyl fluoride evolution and 2 was collected as above. The yield of pure 2 was 58.5 g (88%) along with 8 g of $CF_2(COOCH_3)_2$.

A total of 170 g of 1 was converted (0.36% catalyst requirement by weight).

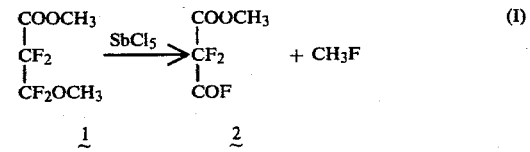

(I)

A mixture of 68.6 g of 1 and 0.67 g of SbCl5 in a still pot when heated to about 100° began to evolve methyl fluoride gas and the temperature began to drop. The mixture was then refluxed at about 88° while 2 was distilled off at a slow rate.

There was recovered 49.5 g (87.9%) of 2 and 4.5 g of CF₂(COOCH₃)₂.

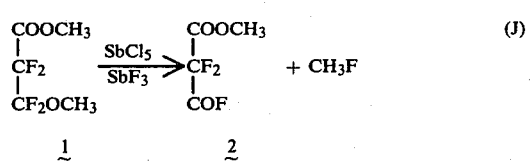

A mixture of 1.38 g of SbCl₅, 1 g of SbF₃ and 5 ml (8 g) of 1 was sealed in a glass tube. Methyl fluoride was evolved at room temperature and after heating 2.5 hours on a steam bath the product analyzed by gas chromatography was 74% (4.9 g) of 2, 0% of 1 and 26% of CF₂(COOCH₃)₂.

(K)–(R) Additional catalysts were used in the conversion of methyl 2,2,3,3-tetrafluoro-3-methoxypropionate (1) to methyl difluoro(fluoroformyl)acetate (2) using a reaction system essentially as described in Example 2C. The catalysts, their amounts, the amounts of reactants employed and products recovered, the reaction temperature and time are tabulated below:

| | CATALYST | | 1 | 2 | | REACTION | |
|---|---|---|---|---|---|---|---|
| | | Wt. | | | | Temp. | Time |
| Ex. | Compd. | (g) | (g) | (g) | (%) | (°C.) | (h) |
| 2K | ZrCl₄ | 1.0 | 67.8 | 49.0 | 88 | 120–135 | 6 |
| 2L | NbF₅ | 1.79 | 676.5 | 544.7 | 98 | 92–130 | 10 |
| 2M | AsF₅ | 7.0 | 185.2 | 138.6 | 91 | 85 | 1 |
| 2N | AlCl₃ | 0.97 | 68.3 | 51.3 | 91.5 | 120 | 3 |
| 2O | HfCl₄ | 1.0 | 71.3 | 52.7 | 90 | 120 | 6 |
| 2P | TaCl₅ | 1.23 | 69.2 | 51.3 | 90 | 120 | 1 |
| 2Q | TiCl₄ | 1.0 | 68.0 | 54.0 | 97 | 115–125 | 0.5 |
| 2R | FeCl₃ | 6.7 | 61.5 | 35.0 | 96 | 135 | 6 |
| 2S | NbI₅ | 1.1 | 69.7 | 56.6 | 99 | 135 | 0.5 |
| 2T | NbBr₅ | 2.7 | 67.0 | 53.1 | 96.5 | 120 | 0.5 |
| 2U | AlI₃ | 8.7 | 61.5 | 47.2 | 93.5 | 125 | 1 |
| 2V | AlBr₃ | 1.95 | 70.3 | 55.2 | 96 | 130 | 3 |
| 2W | TiBr₄ | 4.0 | 64.5 | 49.8 | 94 | 98 | 0.5 |
| 2X | NOSbF₆ | 1.0 | 67.8 | >53.0 | >95 | 70–100 | 0.5 |

EXAMPLE 3

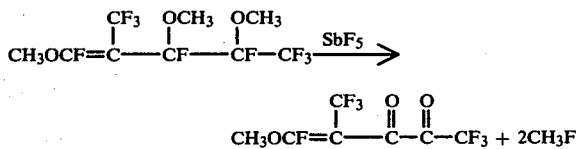

The reaction of the kinetic dimer of hexafluoropropene ((CF₃)₂CFCF=CFCF₃) with sodium methoxide in methanol is reported to give predominantly 1,3,4-trimethoxy-2-trifluoromethyl-1,3,4,5,5,5-hexafluoro-1-pentane (N. Ishikawa and A. Nagashima, Bull. Chem. Soc. Japan, 49 (2), 504 (1976)).

To 14.5 g of antimony pentafluoride in a still pot under nitrogen was added slowly 75 g of the trimethoxy compound prepared as described in the above reference. Methyl fluoride was evolved and the product was distilled, b.p. mostly 32° to 75°/55 mm. This material was then cooled, mixed with an additional 5.5 g of SbF₅ and redistilled. There was obtained 24.5 g of the above methoxy diketone, b.p. 91°/60 mm, refractive index $n_D^{25} = 1.3648$. Infrared 5.40μ and 5.95μ (C=O). The proton and fluorine magnetic resonance were consistent with the above structure, and elemental analysis agreed with the formula C₇H₃F₇O₃.

EXAMPLE 4

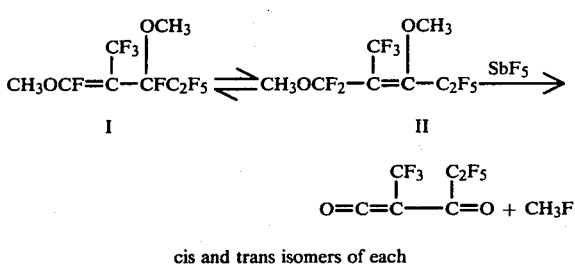

cis and trans isomers of each

The above equilibrium mixture of dimethoxy derivatives was prepared by the reaction of the hexafluoropropene dimer, (CF₃)₂C=CFC₂F₅, with sodium methoxide in methanol, as described by N. Ishikawa and A. Nagashima, Bull. Chem. Soc. Japan, 49 (2), 505 (1976).

The isomeric mixture (73 g) was added to 4.4 g of SbF₅ in a still pot under nitrogen and heated. Methyl fluoride was evolved and there was distilled 42.9 g (66.6%) of the above acylketene, b.p. 80°–81°.

EXAMPLE 5

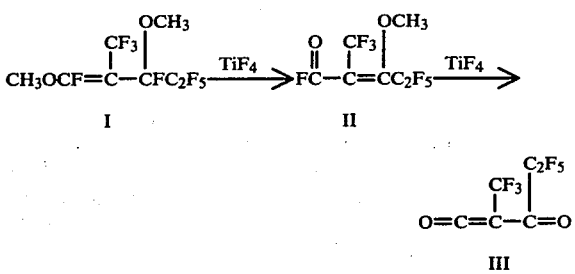

The above methyl ether I (34 g) was added to 2.3 g of TiF₄ in a still pot and the mixture heated. Methyl fluoride was evolved and there was distilled 26.3 g which was largely the acid fluoride, II, b.p. 103°. Structure II was confirmed by IR (5.36μ COF, 5.99μ C=C) and nuclear magnetic resonance, and elemental analysis was consistent with the formula C₇H₃F₉O₂.

Part of the above product (19.6 g) was recharged to the still pot with 2.5 g of TiF₄ and reheated. More methyl fluoride was evolved and 15.7 g of product distilled mostly at 79° and was characterized by infrared as the acylketene III above.

EXAMPLE 6

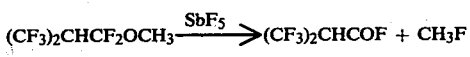

The above ether (77 g), prepared by bubbling perfluoroisobutene into methanol, was placed in a 100-ml 3-neck flask attached to a spinning band still and fitted with a thermometer and dropping funnel. A Dry Ice-acetone trap was attached to the still. After cooling the ether to −40°, 2.23 g of SbF₅ was added and the cooling bath removed. Reaction began (evolution of CH₃F) below room temperature and considerable product was carried into the Dry Ice trap. When evolution of gas was complete, the liquid in the trap was carefully transferred to the pot and distillation then gave 55.3 g of α-hydrohexafluoroisobutyroyl fluoride, b.p. 30° to 33°.

EXAMPLE 7

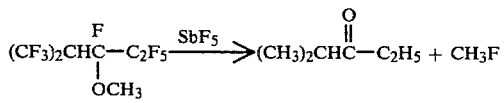

A 100-ml 3-neck flask was attached to a spinning band still, fitted with a thermometer and dropping funnel, evacuated and flushed with nitrogen. The above ether (38 g) was added, cooled with a Dry Ice-acetone bath and then 1.0 g of SbF$_5$ added. While coming to room temperature methyl fluoride was rapidly evolved. When evolution was complete, heat was applied to distill the above ketone, b.p. 60°, 30 g (88%).

The flask was then cooled to room temperature and more ether (30.5 g) added dropwise through the funnel with stirring. Reaction (evolution of CH$_3$F) was vigorous with the insoluble residue in the flask acting as catalyst. When gas evolution was complete, the pot was heated and 20 g of ketone collected. The pot was then cooled and the contents of the Dry Ice-acetone trap attached to the still added and distilled to give an additional 5 g of ketone. The total yield was therefore 57 g (92.7%).

EXAMPLE 8

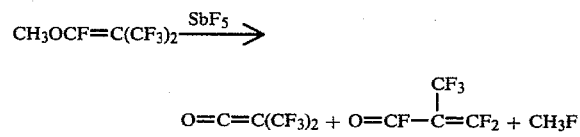

The above methyl ether (29 g) and antimony pentafluoride (2.4 g) were mixed cold in a still pot. Gas (CH$_3$F) was evolved at room temperature and 23 g of material collected in a Dry Ice-acetone trap attached to the still. Redistillation of this material in a low temperature still gave 8.5 g (35.4%) of bis(trifluoromethyl)ketene, b.p. 5° and 9.0 g (37.5%) of perfluoromethacryloyl fluoride, b.p. 52°. The products were further characterized by infrared.

EXAMPLE 9

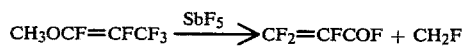

The above methyl ether (20 g), prepared from hexafluoropropene and sodium methoxide, was cooled in a still pot with a Dry Ice-acetone bath and stirred while adding 2.8 g of SbF$_5$. On warming, an exothermic reaction occurred (maximum temp. 30°) and distillation gave 7.8 g, b.p. 70° to 85°. The Dry Ice-acetone trap attached to the still collected 7.5 g of CF$_2$=CFCOF (perfluoroacryloyl fluoride) (b.p. 25°), characterized by infrared.

EXAMPLE 10

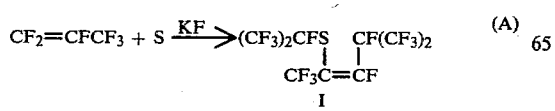

-continued

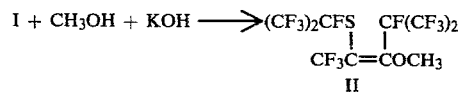

Potassium fluoride (25 g) was vacuum dried in a 3-liter, 3-neck flask by heating with a hot-air gun under vacuum. After cooling and flushing with nitrogen, 64 g (2 m) of sulfur (vacuum dried) and 200 ml of purified dimethylformamide were added, the flask tared, evacuated, pressured with hexafluoropropene (HFP) (maintained automatically at about 740 mm) and vigorously stirred. After heating to 75° to start the reaction, it was exothermic to 83°. It was stopped while still reacting (856 g of HFP absorbed) and started again the next morning after adding 25 g of fresh catalyst. An additional 151 g of HFP was absorbed making a total of 1007 g (6.7 m). The mixture was then washed three times with water and then conc. H$_2$SO$_4$. There was obtained 707 g (75%) of I above (cis and trans isomers); b.p. 130° to 134°.

A solution of 132 g of 85% KOH (2 m) in 500 ml of methanol was cooled to −30° and 250 g (0.5 m) of the vinyl sulfide I added slowly. When addition was complete, cooling was removed and stirring continued. The exothermic reaction was cooled as necessary to keep the temperature below 50°. After stirring for an hour at room temperature, the mixture was poured into cold water, the heavy layer washed with water, dried and distilled. There was obtained 21 g (8.5%), b.p. 65°-70°/8.5 mm, largely II above.

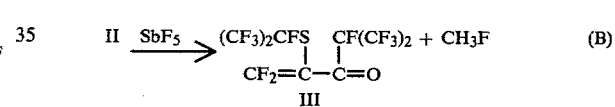

A mixture (100 ml) of products from Part A containing product II was treated with 5 ml of SbF$_5$ and rapidly distilled. This was repeated three times when distillation gave a fraction, 5.7 g, b.p. 110° which was 90% III. IR; 5.70μ (C=O) and 5.95μ (C=C). Fluorine magnetic resonance was consistent with the structure III; elemental and mass spectrometric analysis were consistent with the formula C$_9$F$_{16}$SO.

EXAMPLE 11

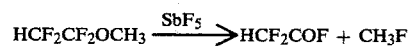

The above ether (32.5 g, prepared from the base-catalyzed addition of methanol to tetrafluoroethylene) in a still pot was cooled in a Dry Ice-acetone bath and 1.81 g of SbF$_5$ was added. It was stirred on a still for 3 h with a Dry Ice-acetone trap attached while coming to room temperature. All but the SbF$_5$ had volatilized into the trap. Redistillation in a low temperature still gave 12.3 g of difluoroacetyl fluoride, b.p. about 0°, characterized by infrared and 13.6 g of recovered starting material, b.p. 33°.

EXAMPLE 12

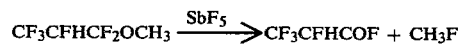

15

The above methyl ether (49.5 g, prepared from the reaction of hexafluoropropene with sodium methoxide in methanol) in a still pot was cooled in a Dry Ice-acetone bath and 2.70 g of SbF$_5$ was added. The mixture was stirred on a still with a Dry Ice-acetone trap attached and the cooling bath removed. Evolution of CH$_3$F was vigorous below room temperature. The mixture was warmed until all of the product had collected in the Dry Ice-acetone trap. Material in the trap was redistilled in a low-temperature still to give 33 g (82%) of 2,3,3,3-tetrafluoropropionylfluoride, b.p. 25°.

EXAMPLE 13

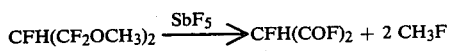

The above ether (15 g, a by-product of the reaction of hexafluoropropene with sodium methoxide in methanol) in a still pot was cooled in a Dry Ice-acetone bath and 2.52 g of SbF$_5$ added. The mixture was stirred on a still with the cooling bath removed. Vigorous evolution of methyl fluoride began below 0°. There was then distilled 8.2 g (84%) of the above diacid fluoride, b.p. 72°.

EXAMPLE 14

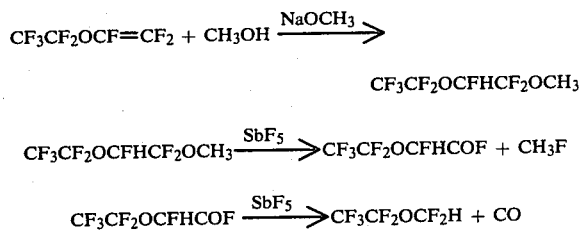

To a stirred solution of 5% sodium methoxide in methanol was added gaseous perfluoroethyl vinyl ether with cooling (40° to 50°). The crude methyl ether product was water-washed and distilled, b.p. 70°.

The above methyl ether (40 g) in a still pot was cooled in Dry Ice and 3.28 g of SbF$_5$ was added. The mixture was stirred and heated on a spinning band still with a Dry Ice-acetone trap attached. Evolution of methyl fluoride was vigorous at room temperature. The distillate and material in the Dry Ice-acetone bath was combined and redistilled in a low temperature still. There was collected 8.1 g (27%) of CF$_3$CF$_2$OCF$_2$H, b.p. mostly −12° and 20.7 g (60%) of CF$_3$CF$_2$OCFH-COF, b.p. 50° to 52°. Structures were confirmed by proton and fluorine magnetic resonance.

EXAMPLE 15

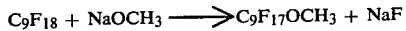

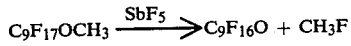

A mixture of 200 ml of methanol and 225 g of hexafluoropropene trimer isomer mixture (C$_9$F$_{18}$, see Brunskill, et al. Chem. Communications, 1444 (1970) of probable structure

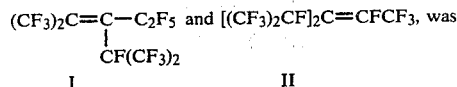

stirred and cooled at −30° to −20° while adding dropwise a solution of 60 g of sodium methoxide in 400 ml of methanol. After coming to room temperature the mixture was poured into water, extracted with methylene chloride, and washed with dilute HCl. Distillation gave 176 g of methoxy derivative, b.p. 80° to 90°/40 mm, a mixture of at least two isomers (containing unsaturated methyl ether, C$_9$F$_{17}$OCH$_3$) by gas chromatography. The unsaturated methyl ether C$_9$F$_{17}$OCH$_3$ appears to arise from structure II above and is thought to have the structure

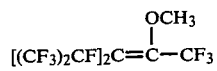

The above mixture (50 g) in a still pot was cooled in an ice bath and 5.16 g of antimony pentafluoride (SbF$_5$) was added. The mixture was heated on a still and vigorous evolution of methyl fluoride began at about 50° C. There was distilled 8.3 g of C$_9$F$_{16}$O vinyl ketone boiling mostly at 100° and 35 g of higher-boiling material which was retreated with 6.05 g of SbF$_5$ and 10.4 g more of the C$_9$F$_{16}$O vinyl ketone distilled. The vinyl ketone absorbed at 5.60μ in the infrared. Elemental analysis was consistent with the formula C$_9$F$_{16}$O. The vinyl ketone is believed to have the structure

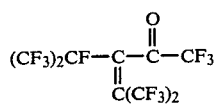

EXAMPLE 16

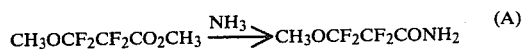

A solution of 140 g (0.74 mol) of methyl 3-methoxytetrafluoropropionate in 100 ml of ether was treated at 0° with 15.3 g (0.90 mol) of NH$_3$. The resulting viscous mixture was stirred at 25° overnight and evaporated to dryness at 25° (10 mm). The crude residue was then recrystallized from ether/hexane to give 123.6 g (95%) of 3-methoxytetrafluoropropionamide, mp 78°-80°. An analytical sample was recrystallized from ether/hexane, m.p. 83° to 85°. IR (KBr): 2.95, 3.02 and 3.10 (NH$_2$), 3.37 and 3.49 (sat'd CH), 5.92 (C=O), 6.19 (NH$_2$), 7.5-10μ (CF, C—O). NMR ((CD$_3$)$_2$(CO): $^1$H 6.67 (broad, 2H, NH$_2$) and 3.66 ppm (s, 3H, OCH$_3$): $^{19}$F −1.20.6 (t, J$_{FF}$ 4.7 Hz, 2F, CF$_2$) and −121.8 ppm (t, J$_{FF}$ 4.7 Hz, of d, J$_{HF}$, 2.1 Hz, 2F, CF$_2$). Elemental analysis was consistent with the formula C$_4$H$_5$F$_4$NO$_2$.

A solution of 52.5 g (0.30 mol) of the amide from Part A in 200 ml of diglyme was stirred at −10° while 47.5 g (0.60 mol) of pyridine and then 63.0 g (0.30 mol) of trifluoroacetic anhydride were added. The cooling bath was removed, and the mixture was stirred at about 25° for 2 h. Evaporation of volatiles to 40° (4.5 mm) gave 42.7 g of crude product, which was distilled to afford 36.5 g (77%) of 3-methoxytetrafluoropropionitrile, b.p. 53°. IR (neat): 3.36 and 3.48 (sat'd CH), 4.42 (CN), 8-10μ (CF, C—O). NMR: $^1$H 3.78 ppm (s, OCH$_3$): $^{19}$F −93.2 (t, $J_{FF}$ 6.3 Hz, 2F, CH$_2$) and −108.8 ppm (t, $J_{FF}$ 6.3 Hz, 2F, CF$_2$). Elemental analysis was consistent with the formula C$_4$H$_3$F$_4$NO.

  (C)

A mixture of 5.5 g of SbF$_5$ and 22 g of 3-methoxytetrafluoropropionitrile prepared as in Part B was refluxed for 0.5 h in a 3-necked flask fitted with a dropping funnel, magnetic stirrer and water condenser to which a Dry Ice-cooled trap was attached. Only a very small amount of material collected in the trap. A total of 13.5 g SbF$_5$ was then added to the refluxing pot through the dropping funnel.

Material collected in the Dry Ice trap was distilled to give 3 g (17%) of NC-CF$_2$COF (2-cyanodifluoroacetyl fluoride), b.p. approximately 0°.

EXAMPLE 17

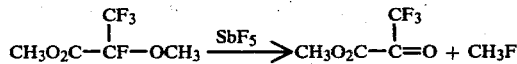

A nitrogen-flushed, 300-ml, 3-neck pot with magnetic stirrer, thermometer, pressure-equalizing dropping funnel and 6-inch vigreux column topped by a Dry Ice-cooled trap and nitrogen bubbler was charged with 100 g of Rimar ® 101, (30 to 35% perfluoro-2(n-butyl)furan, 55-60% perfluoro-2(n-propyl)pyran, 5 to 15% unidentified perfluorinated compounds, product of Rimar SpA, Italy) solvent and 6 g of SbF$_5$, stirred and heated to 95°. Then, 102.8 g of methyl-2-methoxytetrafluoropropionate was added slowly. Gas was evolved. The pot temperature was maintained at 84° to 90°. The gaseous product was collected and identified by IR as largely methyl fluoride.

The residual liquid was cooled to room temperature and distilled through a 3-fit, Pt spinning band column. An amount of 119.3 g of a fraction boiling at 80° was collected and identified by gas chromatography and IR as an azeotrope of Rimer ® 101 and methyl 2-oxo-3,3,3-trifluoropropionate.

EXAMPLE 18

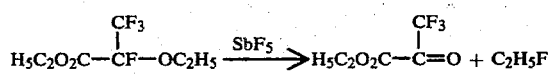

A nitrogen-flushed, 500 ml 3-neck pot, equipped as described in Example 17, was charged with 340.3 g (1.56 mol) of ethyl-2-ethoxytetrafluoropropionate and 19.5 g (0.09 mol) of SbF$_5$. Gas was evolved. The mixture was heated and distilled to give 220 g (83.0% yield) of ethyl trifluoropyruvate, b.p. 88° to 89°. The gaseous product was collected and identified by IR as largely ethyl fluoride.

EXAMPLE 19

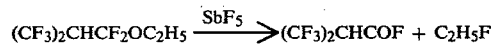

The above ethyl ether (99.2 g, 0.40 mol) was charged to a 125 ml flask equipped as described in Example 6. SbF$_5$ (7.3 g, 0.034 mol) was added, and ethyl fluoride was evolved at room temperature. The mixture was distilled to give 61 g (77.0% yield) of 2-hydrohexafluoroisobutyroyl fluoride, b.p. 30°-33°.

INDUSTRIAL APPLICABILITY

Class 1 to 5 ethers are converted to fluorinated acid fluorides by the process of this invention. Class 6 ethers are converted to ketones which can in turn be converted to acid fluorides by known methods. Said acid fluorides are intermediates to fluorinated vinyl ethers from which copolymers useful as stable oils, greases, elastomers and films may be prepared.

Ethers of Class 3 provide terminally unsaturated acid fluorides which can be copolymerized directly to useful fluoropolymers or converted to vinyl ethers; copolymers prepared from the latter contain thermal double bonds especially useful for curing said copolymers to durable elastomers or shaped articles. Class 4 and 5 ethers provide internal unsaturation which can be similarly utilized as cure sites in copolymers prepared from vinyl ethers derived from Class 4 and 5 ethers.

Ethers of Class 7 provide terminally unsaturated ketones which can be copolymerized to fluorinated copolymers useful as stable oils, greases, elastomers and films.

Preferred ethers in the practice of this invention are of Class 1. Especially preferred are methyl 2,2,3,3-tetrafluoro-3-methoxypropionate (Example 2) and 3-methoxy tetrafluoropropionitrile (Example 16). Said ethers, respectively, provide methyl difluoro(fluoroformyl)acetate, an intermediate in the preparation of fluorinated vinyl ether copolymers which are especially useful as membranes in chlor-alkali electrolysis cells; and cyanodifluoroacetyl fluoride, an intermediate in the preparation of curable fluoroelastomers. Preferred embodiments of this invention are those of Examples 2C, 2F, 2I and 2Q.

COMPARATIVE EXAMPLES 1 to 3

Comparative Examples 1 and 2 demonstrate the impossibility of predicting whether AlCl$_3$, AlBr$_3$ and AlI$_3$ will effectively catalyze fluoroether conversions according to the process of this invention. Comparative Example 3 demonstrates the inoperability of CaCl$_2$ as a catalyst in the process of this invention.

COMPARATIVE EXAMPLE 1

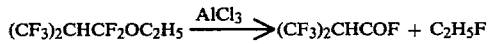

The above ethyl ether, 43 g (0.175 mol), in a 100 ml flask equipped as described in Example 6 was mixed with 1 g (0.0075 mol) of AlCl$_3$. The mixture was refluxed for 17 hours. Material condensed in the attached Dry Ice-acetone trap was combined with residual material in the flask and distilled in a low-temperature still. An amount of 30.8 g of unreacted (CF$_3$)$_2$CHCF$_2$OC$_2$H$_5$ was recovered, together with 9.1 g (26.3% yield) of (CF$_3$)$_2$CHCOF, 2.2 g of C$_2$H$_5$F and 0.1 g of (CF$_3$)$_2$CHCOCl. No improvement in product yield was obtained when the reactants were heated in a sealed tube at 120° for 4 hours.

COMPARATIVE EXAMPLE 2

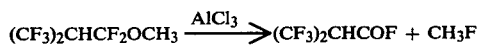

The above methyl ether, 48.5 g (0.209 mol), and 1 g of AlCl$_3$ were refluxed together for 15 hours and treated as described in Comparative Example 1. An amount of 43.8 g of unreacted (CF$_3$)$_2$CHCF$_2$OCH$_3$ was recovered, together with 1.1 g of (CF$_3$)$_2$CHCOF (2.7% yield) and 0.75 g of CH$_3$F. No improvement in product was obtained when the reactants were heated in a sealed tube at 120° for 4 hours.

COMPARATIVE EXAMPLE 3

Calcium chloride, 33.3 g (0.3 mol), was added to a 100-ml 3-neck flask attached to a 46 cm spinning band distillation unit. Vacuum (1 mm Hg) was applied and the flask was flame-heated at about 300° C. to dry the CaCl$_2$. When cool, the system was flushed with nitrogen, the flask was fitted with a thermometer and stirring magnet, and 57.0 g of methyl (3-methoxytetrafluoropropionate) CH$_3$OCF$_2$CF$_2$CO$_2$CH$_3$.

On heating the flask, the temperature rose steadily to the boiling point of the starting ether (134° C.). Only the starting ether was recovered, by distillation. No reaction products were detected. Had reaction occurred, the expected product methyl difluoro(fluoroformyl)acetate, FOCCF$_2$CO$_2$CH$_3$, would have distilled over at its boiling point, 82°.

The embodiments of the invention in which an exclusive property or privilege is claimed are defined as follows:

1. A method of preparing fluorinated carbonyl compounds which comprises contacting a fluorinated methyl or ethyl ether containing at least one methoxylated carbon atom-containing group selected from the group consisting of —CF$_2$OR$^3$, 

=CFOR$^3$, 

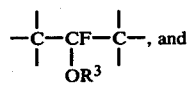

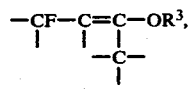

wherein R$^3$ is CH$_3$ or C$_2$H$_5$, with a catalyst selected from the group consisting of
SbX$_5$, TaX$_5$, NbX$_5$, AsX$_5$, BiX$_5$, TiX$_4$, ZrX$_4$, HfX$_4$, FeX$_3$,
mixtures of SbX$_3$ and SbX$_5$, ZM'X'$_6$, and mixtures of ZM'X'$_6$ and M'X$_5$ where M' is Sb or As; X, independently, is F, Cl, Br or I; X' is F or Cl; and Z is H, NO, O$_2$, alkali metal or NY$_4$ were Y, independently, is H or alkyl of 1 to 6 carbon atoms at a temperature of −20° to 200° C.

2. The method of claim 1 in which the contacting is carried out at a temperature of −10° to 150° C.

3. The method of claim 2 in which the catalyst is SbF$_5$.

4. The method of claim 2 in which the catalyst is SbCl$_5$.

5. The method of claim 2 in which the catalyst is a mixture of SbF$_5$ and HSbF$_6$.

6. The method of claim 2 in which the catalyst is TiCl$_4$.

7. The method of claim 2 in which the fluorinated methyl or ethyl ether is a saturated terminal ether of the formula

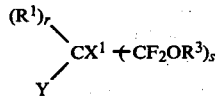

wherein
X$^1$ is —H or —F;
Y is —F or —CF$_3$;
r is 0 or 1;
s is 1 or 2 and r+s=2;
R$^1$ is —F, —Cl, —Br, —SO$_2$F, —COF, —OCH$_3$, —CN, —CO$_2$H, —CO$_2$CH$_3$, —OC$_6$F$_5$, —OR, —SR, or —R, where R is a perfluorinated alkyl of 1 to 8 carbon atoms, linear or branched, interruptable with ether oxygen or keto groups, and optionally contains functional substituents selected from the group consisting of —F, —Cl, —Br, —SO$_2$F, —COF, —OCH$_3$, —CN, —CO$_2$H, —CO$_2$CH$_3$, and —OC$_6$F$_5$.

8. The method of claim 2 in which the fluorinated ether is R$^3$O$_2$CCF$_2$CF$_2$OR$^3$.

9. The method of claim 2 in which the fluorinated ether is NCCF$_2$CF$_2$OR$^3$.

10. The method of claim 2 in which the fluorinated ether is an internally unsaturated terminal ether of the formula

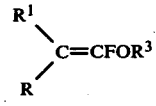

wherein
R$^1$ is —F, —Cl, —Br, —SO$_2$F, —COF, —OCH$_3$, —CN, —CO$_2$H, —CO$_2$CH$_3$, —OC$_6$F$_5$, —OR, —SR, or —R; and
R is a perfluorinated alkyl of 1 to 8 carbon atoms, linear or branched, interruptable with ether oxygen or keto groups, and which optionally contains functional substituents selected from the group consisting of —F, —Cl, —Br, —SO$_2$F, —COF, —OCH$_3$, —CN, —CO$_2$H, —CO$_2$CH$_3$, —OC$_6$F$_5$.

11. The method of claim 2 in which the fluorinated ether is an unsaturated internal ether of the formula

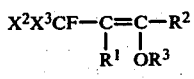

wherein
X$^2$ and X$^3$ are the same or different and are selected from —H, —F, or —Cl;

$R^1$ is —F, —Cl, —Br, —SO$_2$F, —COF, —OCH$_3$, —CN, —CO$_2$H, —CO$_2$CH$_3$, —OC$_6$F$_5$, —OR, —SR or —R, where R is a perfluorinated alkyl of 1 to 8 carbon atoms, linear or branched, interruptable with ether oxygen or keto groups, and which optionally contains functional substituents selected from the group consisting of —F, —Cl, —Br, —SO$_2$F, —COF, —OCH$_3$, —CN, —CO$_2$H, —CO$_2$CH$_3$, —OC$_6$F$_5$; and $R^2$ is a perfluoroalkyl of 1 to 8 carbon atoms.

12. A method of preparing the carbonyl compound, $R^3O_2CCF_2COF$, wherein $R^3$ is CH$_3$ or C$_2$H$_5$, by contacting a fluorinated methyl or ethyl ether, $R^3O_2CCF_2CF_2OR^3$, with AlCl$_3$, AlBr$_3$ or AlI$_3$ at a temperature of 60° to 140° C.

* * * * *

UNITED STATES PATENT OFFICE
CERTIFICATE OF CORRECTION

PATENT NO. : 4,357,282
DATED : November 2, 1982
INVENTOR(S) : Daniel G. Anderson, David C. England and Alwin S. Milian, Jr.

It is certified that error appears in the above-identified patent and that said Letters Patent are hereby corrected as shown below:

In Example 7, Column 13, line 7, the first formula to the right of the arrow should read:

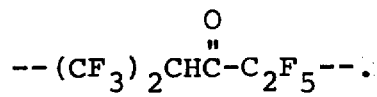

$$-\!-(CF_3)_2CH\overset{O}{\overset{\|}{C}}-C_2F_5-\!-.$$

Signed and Sealed this

Seventeenth Day of May 1983

[SEAL]

Attest:

DONALD J. QUIGG

Attesting Officer    Acting Commissioner of Patents and Trademarks